United States Patent
Tanida et al.

(10) Patent No.: US 6,620,834 B1
(45) Date of Patent: Sep. 16, 2003

(54) MEDICINAL COMPOSITIONS FOR TREATING COLORECTAL CANCER

(75) Inventors: Norifumi Tanida, Ibaraki (JP); Takeshi Goto, Ibaraki (JP); Naoko Tomizawa, Ibaraki (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 10/019,469

(22) PCT Filed: Jun. 30, 2000

(86) PCT No.: PCT/JP00/04327

§ 371 (c)(1),
(2), (4) Date: Apr. 15, 2002

(87) PCT Pub. No.: WO01/02014

PCT Pub. Date: Jan. 11, 2001

(30) Foreign Application Priority Data

Jul. 2, 1999 (JP) ............................................. 11-188408

(51) Int. Cl.$^7$ ................ A61K 31/415; A61K 31/495; A61K 31/50; A61K 31/405; A61K 31/38; A61K 31/34

(52) U.S. Cl. ................ 514/406; 514/252.06; 514/386; 514/415; 514/437; 514/438; 514/461

(58) Field of Search ................ 514/406, 252.06, 514/386, 415, 437, 438, 461

(56) References Cited

U.S. PATENT DOCUMENTS

| | | | |
|---|---|---|---|
| 5,171,580 A | 12/1992 | Iamartino et al. | 424/490 |
| 5,654,004 A | 8/1997 | Okayama et al. | 424/479 |
| 6,245,797 B1 * | 6/2001 | Winokur | 514/406 |
| 2002/0086894 A1 * | 7/2002 | Kindness et al. | 514/403 |

FOREIGN PATENT DOCUMENTS

| | | |
|---|---|---|
| BE | 903 502 | 2/1985 |
| EP | 0 049 590 A2 | 9/1981 |
| EP | 0 225 189 A2 | 11/1986 |
| EP | 0 754 452 A2 | 1/1997 |
| EP | 0 919 228 A1 | 6/1999 |
| JP | WO 90/13286 | 11/1990 |
| JP | 10 147600 A | 6/1998 |
| WO | WO 83/00435 | 2/1983 |
| WO | WO 94/10983 | 5/1994 |
| WO | WO 95/28963 | 11/1995 |

OTHER PUBLICATIONS

Agarwal et al., "Lovastatin Augments Sulindac–Induced Apoptosis in Colon Cancer Cells and Potentiates Chemopreventive Effects of Sulindac", *Gastroenterology* 1999 117:838–847.

Goldman et al., "Meloxicam inhibits the growth of colorectal cancer cells", *Carcinogenesis* 1998 19 (12) :2195–2199.

Narisawa et al., "Prevention of 1,2–dimethylhydrazine–induced colon tumorigenesis by HMG–CoA reductase inhibitors, pravastatin and simvastatin, in ICR mice", *Carcinogenesis* 1994 15 (9) :2045–2048.

Sacks et al., "The Effect of Pravastatin on Coronary Events After Myocardial Infarction in Patients with Average Cholesterol Levels", *The New England Journal of Medicine* 1996 335(14) :1001–1009.

Taketo M.M., "COX–2 and colon cancer",*Inflamm. res.* 1998 47 (2) :S112–S116.

* cited by examiner

*Primary Examiner*—Jerome D. Goldberg
(74) *Attorney, Agent, or Firm*—Licata & Tyrrell P.C.

(57) ABSTRACT

Medicinal compositions for colorectal cancer to be administered to the large intestine by taking advantage of preparations disintegrating in the large intestine, characterized by containing a cyclooxygenase inhibitor and an HMG-CoA reductase inhibitor. These compositions are appropriate for inhibiting the postoperative liver metastasis and recurrence of colorectal cancer.

2 Claims, 1 Drawing Sheet

MEDICINAL COMPOSITIONS FOR TREATING COLORECTAL CANCER

TECHNICAL FIELD

The invention relates to a pharmaceutical composition to be administered to the large intestine for treating a colorectal cancer.

BACKGROUND ART

In cancer therapy the surgical treatment is the mainstream at present. However, in order to improve the performance of the surgical treatment further, an ancillary use of chemotherapy is indispensable. Since cases of cancer metastasis to the liver or lung due to a hemokinetic metastasis from, in particular, the colorectal cancer is frequently observed, a postoperative ancillary chemotherapy has become essential. For the chemotherapy aiming to inhibit the postoperative metastasis and recurrence of cancer, usually an oral anticancer agent represented by 5-fluorouracil is mainly used. In case of using such an anticancer agent expecting the metastasis inhibition or recurrence prevention, a medicine-taking period for one year or more is necessary, though the present situation is that the medication is compelled to be abandoned owing to the development of a strong digestive tract disorder or a systemic side effect such as a severe myelosuppression. Therefore, naturally there is limitation for achieving the above object only by the chemotherapy mainly using an anticancer agent.

Further, in case of making the chemotherapy aim to prevent especially the postoperative liver metastasis of colorectal cancer, it is important to carry out a drug delivery from the mesenteric vein to the portal in a metastasis route of cancer cells and to maintain a drug concentration in the portal blood.

From the above viewpoints, it is considered to be effective that a drug with a low side effect except an anticancer agent, which is appropriate for inhibiting the metastasis and can be administered for a long period, is directly administered to the large intestine. As described above, from the above viewpoints of a dosage form which can be administered for a long period at home, a dosage form like an oral preparation is naturally preferable.

At present, among the representative agents being developed as a metastasis inhibitor there are drugs to inhibit the cell adhesion between cancer cells and vascular endothelial cells or their interaction, being antibodies for cell adhesion molecules such as fibronectin, ICAM-1, integrin, selectin, cadherin and laminin, peptide fragments or antisenses (JP, A, 10-147600, etc.). Although these drugs inhibit cell adhesion or metastasis in a specific way, there is only an administration method such as an intravenous administration owing to high molecular oligopepteides or oligonucleotides in all, being not apt to a home treatment because of inferior convenience.

Meanwhile, in drugs of low molecular weight, nonsteroidal antiinflammatory agents represented by aspirin or acetaminophen having a cyclooxygenase inhibitory activity are reported to have action to inhibit carcinogenesis, cancer recurrence and vascularization (Carcinogenesis., 19(12): 2195–9, 1998, Inflammation Research., 47 Suppl 2:S112–6, 1998, etc.). Although these drugs can be administered orally because they are low molecular weight drugs, it is necessary to increase the dosage to obtain an expected effect, while a continuous administration produces digestive tract disorders in a high frequency.

Although there is a possibility that a cyclooxygenase inhibitor is put into practice as a medicine for inhibiting the cancer recurrence and cancer metastasis, the present situation is that it is not put into practice owing to its weak activities by itself and problems of side effects against the digestive tract system.

Although various drug developments in which a postoperative ancillary chemotherapy aiming at inhibiting the metastasis and recurrence of cancer are tried as described above, a drug which has a high effectiveness and can be orally administered to make the administration of a long period possible has not been developed to date. Although oral anticancer agents of 5-FU type currently used in the postoperative anchillary chemotherapy could also be administered orally in a simple way, a strong digestive tract disorder or myelosuppression which the anticancer agents have would become problems. Although trials have also made to administer drugs such as a live bacteria preparation or B-carotene low in toxicity aiming at inhibiting the cancer recurrence, it can hardly be said at present that they have a sufficient effect.

DISCLOSURE OF THE INVENTION

Consequently, the object of the invention is to solve the above problems and to provide a medicinal composition for treating colorectal cancer to be administered to the large intestine which is most appropriate for inhibiting the postoperative liver metastasis and recurrence of colorectal cancer using a preparation disintegrating in the large intestine.

The inventors made extensive researches to solve the above problems and consequently found out that the cancer metastasis inhibitory effect was synergistically increased by mixing a cyclooxygenase inhibitor having a little metastasis inhibitory and vascularization inhibitory action with an HMG-CoA reductase inhibitor showing almost no metastasis inhibitory effect by itself, making it possible to improve sharply a surviving rate of prognosis, and accomplished the invention.

Namely, the invention relates to a medicinal composition for treating colorectal cancer, characterized in that a cyclooxygenase inhibitor and an HMG-CoA reductase inhibitor are mixed.

The invention also relates to the above medicinal composition for treating colorectal cancer, characterized in that the mixing ratio of a cyclooxygenase inhibitor and an HMG-CoA reductase inhibitor is 1:0.1–1:5.

The invention also relates to the above medicinal composition for treating colorectal cancer, characterized in that the cyclooxygenase inhibitor is a nonsteroidal antiinflammatory agent.

Further, the invention relates to the above medicinal composition for treating colorectal cancer, characterized in that the nonsteroidal antiinflammatory agent is selected from loxoprofen sodium, ketoprofen, isopropyl antipyrine, antipyrine, phenacetin, tolfenamic acid, mefenamic acid, ethenzamide, sulpyrine, fenbufen, piroxicam, ibprofen, naproxen, meclophenamate, flurbiprofen, diclofenac, sulindac, aspirin, salicylic acid, acetaminophen, meloxicam, nimesulide, etodlac, nabumeton, celecoxib and rofecoxib.

The invention also relates to the above medicinal composition for treating colorectal cancer, characterized in that the HMG-CoA reductase inhibitor is one or more selected from pravastatin, simvastatin, lovastatin, fluvastatin, atrovastatin and cerivastatin.

The invention also relates to a preparation reaching to the large intestine, comprising the above composition.

Further, the invention relates to a preparation disintegrating in the large intestine, comprising the above composition.

Embodiment of the Invention

Figure 1:
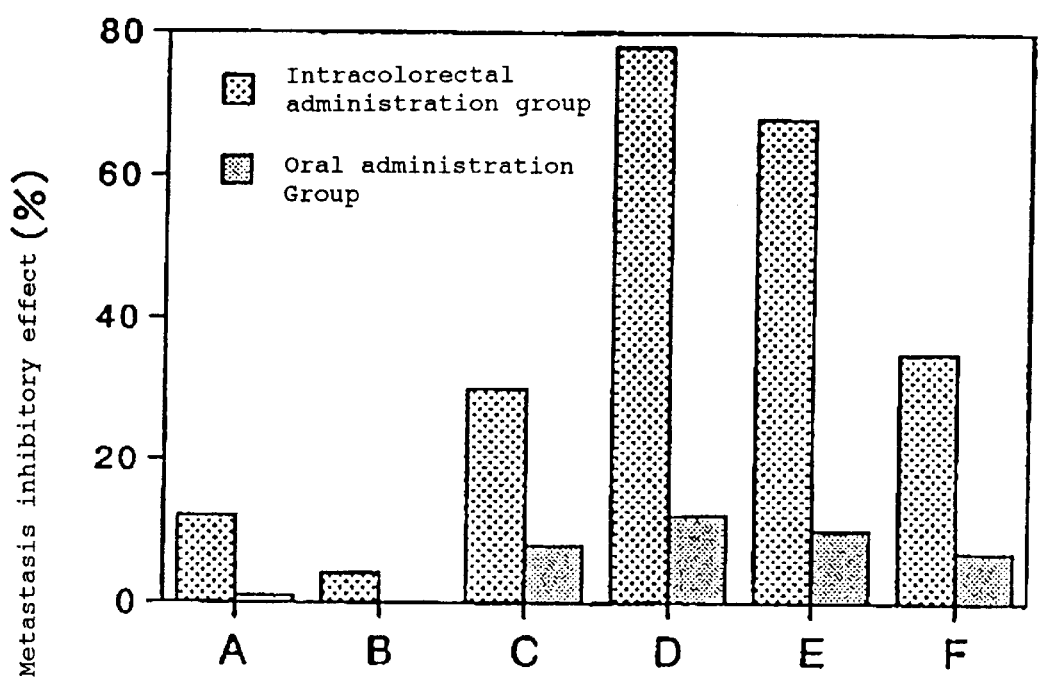
FIG. 1 is the graph showing the metastasis inhibitory ratios in each solution when the liver metastasis inhibitory effect in Yoshida's sarcoma rat model bearing a colorectal cancer was evaluated using the drug-mixed solution prepared in the example 1.

In the following is explained are embodiments of the invention.

As a preferable embodiment, the mixing ratio of a cyclooxygenase inhibitor and an HMG-CoA reductase inhibitor is 1:0.1–1:5, more preferably 1:0.5–1:2. Namely, the effect of each drug which alone has only a low metastasis inhibitory effect is greatly improved by a synergistic action adjusting the mixing ratio, and it becomes possible to improve remarkably a surviving rate of prognosis by utilizing it as a postoperative ancillary chemotherapy for colorectal cancer.

In the invention, as an HMG-CoA reductase inhibitor preferably used are simvastatin, pravastatin, lovastatin, fluvastatin, atrovastatin and cerivastatin, or the salts thereof.

As a cyclooxygenase inhibitor also preferably used are nonsteroidal antiinflammatory agents represented by loxoprofen sodium, ketoprofen, isopropyl antipyrine, antipyrine, phenacetin, tolfenamic acid, mefenamic acid, ethenzamide, sulpyrine, fenbufen, piroxicam, ibprofen, naproxen, meclophenamate, flurbiprofen, diclofenac, sulindac, aspirin, salicylic acid,acetaminophen, meloxicam, nimesulide, etodlac, nabumeton and the like, or the salts thereof. More preferably, inhibitors represented by meloxicam, nimesulide, etodlac, nabumeton, celecoxib and rofecoxib to inhibit selectively cyclooxygenase-2 are used.

Further, in the invention, by applying an HMG-CoA reductase inhibitor and a cyclooxygenase inhibitor to an oral preparation disintegrating in the large intestine, a metastasis inhibitory and cancer recurrence inhibitory effect can be exerted without developing not only cholesterol lowering action and antiinflammatory action which are their original pharmacological effects but also a digestive tract disorder and the like which are those drugs' side effects. Namely, in case of administering orally these oral preparations to a post operative patient of colorectal cancer who becomes a subject, a drug delivery in a high dose along the metastasis route of colorectal cancer becomes possible, and therefore, comparing with simple oral preparations in which drugs are absorbed in many cases before reaching to the large intestine of the target site, a cholesterol lowering action and an antiinflammatory action which are the original pharmacological effects of each drug contained in the preparation is not developed, though on the contrary there is no development of the side effects and a much higher effect can also be expected on the cancer metastasis inhibition and recurrence protection.

One possibility as the synergistic action mechanisms for mixing these drugs is that a nonsteroidal antiinflammatory agent having the cyclooxygenase inhibitory activity and an HMG-CoA reductase inhibitor inhibit on the one hand the growth of vascular endothelial cells becoming a new blood vessel in cancer tissue, the HMG-CoA reductase inhibitor inhibits the development of t-PA (tissue plasminogen activator) in vascular endothelial cells and reduces the plasmin activity to dissolve fibrin clots, and therefore, the formation of clot produces an occlusion state when a slight disorder in the new blood vessel occurs. It is considered that it results in inhibiting engraftment of the cancer cells in an organ or tissue.

Since all these mixed drugs consist of low molecular drugs, they will become the most suitable composition for the cancer therapy to be administered to the large intestine for which oral preparation can be prepared.

A medicinal composition for treating colorectal cancer of the invention aiming at administration in the large intestine is favorably prepared as an oral preparation disintegrating in the large intestine. As preparations reaching to the large intestine known are, for example, an oral preparation targeting the large intestine, which is prepared by combining a polymer soluble only at a pH of 5.5 or above with an insoluble polymer (EP, 49590); a solid oral preparation coated with a suitable amount of an anionic copolymer soluble at a pH of 7.0 or above (trade name: Eudragit S, a product of Röhm) (WO83/00435); an oral preparation coated with a mixture comprising an anionic copolymer soluble at a pH of 7.0 or above (trade name: Eudragit S, a product of Röhm) and a methacrylate copolymer difficultly soluble in water (trade name: Eudragit RS, a product of Röhm) (EP, 225189); an osmotic pressure pump preparation coated with an enteric coating polymer (BE, 903502); an oral preparation, reaching to the large intestine, covered with an inner coat soluble at a pH of 7.0 or above, an intermediate coat made of a gelatinized polymer, and an acid-resistant outer polymer coat soluble at a pH of 5.5 or above (JP, A, 4-501411); and so forth. Some of the colorectal delivery art using a coating polymer for a pharmaceutical additive have been reported (WO90/13286, JP, A, 9-87169, WO95/28963). The inventors also proposed an oral pharmaceutical preparation with a high specificity for the large intestine, releasing in the lower digestive tract (WO94/10983, JP, A, 10-152431). This is characterized in that it consists of a double-coated structure in which comparatively moulded tablets or capsules, which are filled with granules, powders or liquids, are made cores and coated with an inner layer consisting of a cationic copolymer and an outer layer consisting of an anionic polymer. This preparation is extremely excellent in specificity for the large intestine, making it possible to carry out the release of a drug targeted to the large intestine more exactly and more rapidly.

Using these preparations disintegrating in the large intestine the invention has made it possible to deliver a mix composition of a cyclooxygenase inhibitor and an HMG-CoA reductase inhibitor for treating colorectal cancer to the large intestine with an intact state, not making it being absorbed in the small intestine. Owing to this, not only a cholesterol lowering action and an antiinflammatory action which are their original pharmacological effects but also a digestive tract disorder and the like are not developed, making a drug delivery in a high dose along the postoperative metastasis route of colorectal cancer possible, and it becomes possible to obtain an excellent metastasis inhibitory and cancer recurrence inhibitory effect, wherefore such a preparation is more preferable to attain the intended objects of the invention.

Illustrative of pharmacologically active substances which canbeutilized here are the followings. As an HMG-CoA reductase inhibitor preferably used are simvastatin, pravastatin, lovastatin, fluvastatin, atrovastatin and cerivastatin, or the salts thereof. Nonsteroidal antiinflammatory agents represented by loxoprofen sodium, ketoprofen, isopropyl antipyrine, antipyrine, phenacetin, tolfenamic acid, mefenamic acid, ethenzamide, sulpyrine, fenbufen, piroxicam, ibprofen, naproxen, meclophenamate, flurbiprofen, diclofenac, sulindac, aspirin, salicylic acid, acetaminophen, meloxicam, nimesulide, etodlac, nabumeton, celecoxib, rofecoxib and the like, or the salts thereof are also used preferably. More preferably, inhibitors represented by meloxicam, nimesulide, etodlac, nabumeton, celecoxib and rofecoxib which inhibit selectively cyclooxygenase-2 are also used. Further, as to the HMG-CoA reductase inhibitor and the cyclooxygenase inhibitor, one or more species of each can be combined and mixed.

The medicinal composition for treating colorectal cancer to be administered to the large intestine in the invention can be prepared by mixing appropriate excipients, humectants and disintegrators together with the above pharmacologically active substances. Specifically, after tablets are manufactured by mix of pharmacological substances and an excipient, coating is made, and in case of aiming to inhibit the metastasis of colorectal cancer by use of them as a preparation disintegrating in the large intestine, it is considerably improved in terms of the side effect and the effect compared with drugs used in the postoperative ancillary chemotherapy including currently used anticancer agents.

As explained above in detail, by administration of the mix preparation of a cyclooxygenase inhibitor and an HMG-CoA reductase inhibitor in the large intestine the cancer metastasis inhibitory effect is distinctly improved, and by use of it as a postoperative ancillary chemotherapy for colorectal cancer, it will become possible to improve remarkably a surviving rate of prognosis.

EXAMPLE

In the following, the medicinal compositions for treating colorectal cancer to be administered to the large intestine in the invention is explained in more detail and concretely by the examples, the comparative examples and the test examples. The invention, however, is not limited to these.

Example 1

The solution was prepared in which pravastatin and aspirin were mixed in the mixing ratio below, and the pharmacological evaluation was carried out in the liver metastasis model of rat colorectal cancer.
Formula A Aspirin Single administration
Formula B Pravastatin Single administration
Formula C Aspirin:Pravastatin=1:0.1 (mole ratio) Mix solution
Formula D Aspirin:Pravastatin=1:0.5 (mole ratio) Mix solution
Formula E Aspirin:Pravastatin=1:1 (mole ratio) Mix solution
Formula F Aspirin:Pravastatin=1:5 (mole ratio) Mix solution The liver metastasis inhibitory effect was evaluated in the following procedure by use of the mix solution prepared in the example 1.

Donryu strain rats (8 weeks old) were used. Under a sodium pentobarbital anesthesia a catheter was inserted from the ileocecum into the colon, and the plug was put out from the back part and fixed. At the same time Yoshida's sarcoma ($1.5 \times 10^6$ cells/30 µl/rat) was injected to the sigmoid subserous.

The mix solution prepared in the example 1 was administered intra-colon or orally for 5 days from the next day after the surgery, and at day 6 a pathologic autopsy was made.

When the test on day 6 was finished, rats were killed by bleeding for a pathologic autopsy. The liver was isolated from each individual, fixed by a neutral buffered formalin solution, and a tissue section was then prepared to obtain histopathological findings. The metastasis inhibitory ratio was calculated comparing with the engraftment ratio of the cancer cells in the control group.

The results are shown in FIG. 1. A means the aspirin single administration group; B means the pravastatin single administration group; C means the mix drug solution administration group of aspirin and pravastatin (1:0.1); D means the mix drug solution administration group of aspirin and pravastatin (1:0.5); E means the mix drug solution administration group of aspirin and pravastatin (1:1); F means the mix drug solution administration group of aspirin and pravastatin (1:5).

Upon comparison of the liver metastasis inhibitory effect by the mix solution of each drug, the metastasis inhibitory effect was hardly observed in aspirin or pravastatin alone, though the remarkable liver metastasis inhibitory effect was observed in the solution mixed with these drugs. However, in the oral administration group the metastasis inhibitory effect was hardly observed even in the mix solution.

Based on the above results it became apparent that the remarkably high liver metastasis inhibitory effect of cancer cells was shown by directly administering the solution mixed with aspirin and pravastatin in the given mole ratio.

Example 2

The following mix solution was prepared using pravastatin or simvastatin as an HMG-CoA reductase inhibitor and as a cyclooxygenase-2 inhibitor using meloxicam, nimesulide, etodlac, nabumeton, celecoxib or rofecoxib which are cyclooxygenase-2 inhibitors.
Formula 1 Meloxicam:Pravastatin=1:0.5 (mole ratio) Mix solution
Formula 2 Meloxicam:Pravastatin=1:1 (mole ratio) Mix solution
Formula 3 Etodlac:Simvastatin=1:0.5 (mole ratio) Mix solution
Formula 4 Etodlac:Simvastatin=1:1 (mole ratio) Mix solution
Formula 5 Nimesulide:Pravastatin=1:0.5 (mole ratio) Mix solution
Formula 6 Nimesulide:Pravastatin=1:1 (mole ratio) Mix solution
Formula 7 Nabumeton:Simvastatin=1:0.5 (mole ratio) Mix solution
Formula 8 Nabumeton:Simvastatin =1:1 (mole ratio) Mix solution
Formula 9 Celecoxib:Pravastatin=1:0.5 (mole ratio) Mix solution
Formula 10 Celecoxib:Pravastatin=1:1 (mole ratio) Mix solution
Formula 11 Rofecoxib:Pravastatin=1:0.5 (mole ratio) Mix solution
Formula 12 Rofecoxib:Simvastatin=1:1 (mole ratio) Mix solution

INDUSTRIAL APPLICABILITY

Because the medicinal compositions for treating colorectal cancer according to the invention have an excellent cancer-metastasis inhibitory effect, it is possible to improve remarkably a surviving rate of prognosis using them in a postoperative ancillary chemotherapy for colorectal cancer. Further, because they do not develop a side effect such as a digestive tract disorder even carrying out an oral administration and can deliver drugs to the target site in a high concentration, they can be used for a long period administration at home. Therefore, the invention has an excellent technical value in pharmaceutical industries.

What is claimed is:

1. A method of treating or preventing colon cancer in a patient in seed thereof comprising administering the medicinal composition comprising synergistic effective amounts of cyclooxygenase inhibitors and HMG-CoA reductase inhibitors wherein the cyclooxygenase inhibitors and HMG-CoA reductase inhibitors are released in the large intestine of said patient.

2. A method of treating or preventing colon cancer in a patient according to claim 1 wherein the medicinal composition in an oral preparation is orally administered and wherein the cyclooxygenase inhibitors and HMG-CoA reductase inhibitors are released in the large intestine of a patient.

* * * * *